(12) United States Patent
Hassan et al.

(10) Patent No.: US 8,450,539 B2
(45) Date of Patent: May 28, 2013

(54) HIGH SHEAR PROCESS FOR PRODUCING MICRONIZED WAXES

(75) Inventors: Abbas Hassan, Sugar Land, TX (US); Aziz Hassan, Sugar Land, TX (US); Gregory G. Borsinger, Chatham, NJ (US)

(73) Assignee: H R D Corporation, Houston, TX (US)

( * ) Notice: Subject to any disclaimer, the term of this patent is extended or adjusted under 35 U.S.C. 154(b) by 166 days.

(21) Appl. No.: 12/613,916

(22) Filed: Nov. 6, 2009

(65) Prior Publication Data

US 2010/0125157 A1 May 20, 2010

Related U.S. Application Data

(60) Provisional application No. 61/112,236, filed on Nov. 7, 2008.

(51) Int. Cl.
*B01F 7/00* (2006.01)
*C08L 91/06* (2006.01)

(52) U.S. Cl.
USPC ....... 585/9; 208/20; 208/21; 208/24; 507/103

(58) Field of Classification Search
USPC .................................. 585/9; 208/20, 21, 24
See application file for complete search history.

(56) References Cited

U.S. PATENT DOCUMENTS

| | | |
|---|---|---|
| 3,432,483 A | 3/1969 | Peoples et al. |
| 3,600,328 A | 8/1971 | Lieffers |
| 3,887,167 A | 6/1975 | Irwin |
| 3,997,489 A | 12/1976 | Coker |
| 4,687,339 A | 8/1987 | Seeger |
| 4,822,603 A | 4/1989 | Farris et al. |
| 4,857,578 A * | 8/1989 | Hall ............................... 524/488 |
| 5,389,136 A * | 2/1995 | Danner ......................... 106/271 |
| 5,538,191 A | 7/1996 | Holl |
| 5,643,984 A | 7/1997 | Mueller et al. |
| 5,741,850 A | 4/1998 | Hosokawa et al. |
| 5,800,604 A * | 9/1998 | Berger .......................... 106/270 |
| 5,877,350 A | 3/1999 | Langer et al. |
| 5,882,114 A | 3/1999 | Fukuyo et al. |
| 5,959,194 A * | 9/1999 | Nenniger ..................... 73/53.01 |
| 5,965,676 A | 10/1999 | Anan |
| 6,066,250 A * | 5/2000 | Kinjo .............................. 208/24 |

(Continued)

FOREIGN PATENT DOCUMENTS

| | | |
|---|---|---|
| EP | 0227430 | 7/1987 |
| WO | 95/30736 A1 | 11/1995 |
| WO | 02064708 A2 | 8/2002 |
| WO | 2010054197 A3 | 5/2010 |

OTHER PUBLICATIONS

Gogate et al., "Cavitation: A Technology on the Horizon," Current Science 91 (No. 1): 35-46 (2006) (12 pgs.).

(Continued)

*Primary Examiner* — Ellen McAvoy
(74) *Attorney, Agent, or Firm* — Porter Hedges LLP; Timothy S. Westby

(57) ABSTRACT

A method and system for producing dispersed waxes, including a high shear mechanical device. In one embodiment, the method comprises forming a dispersion of wax globules in a carrier liquid in a high shear device prior to implementation in a waxy product. In another instance the system for producing waxy products comprises a high shear device for dispersing wax in a carrier liquid.

19 Claims, 3 Drawing Sheets

U.S. PATENT DOCUMENTS

| | | | |
|---|---|---|---|
| 6,368,366 B1 | 4/2002 | Langer et al. | |
| 6,368,367 B1 | 4/2002 | Langer et al. | |
| 6,383,237 B1 | 5/2002 | Langer et al. | |
| 6,431,253 B1 * | 8/2002 | Kinjo | 164/5 |
| 6,530,964 B2 | 3/2003 | Langer | |
| 6,742,774 B2 | 6/2004 | Holl | |
| 6,761,764 B2 * | 7/2004 | Krendlinger et al. | 106/502 |
| 6,875,549 B2 * | 4/2005 | Yamazaki et al. | 430/106.1 |
| 7,556,679 B2 | 7/2009 | Lee et al. | |
| 7,622,031 B2 * | 11/2009 | Seven et al. | 208/20 |
| 7,662,272 B2 * | 2/2010 | Patel et al. | 208/20 |
| 7,686,939 B2 * | 3/2010 | Patel et al. | 208/20 |
| 7,696,270 B2 * | 4/2010 | Lobo et al. | 524/277 |
| 7,794,533 B2 | 9/2010 | Ichikawa et al. | |
| 2003/0043690 A1 | 3/2003 | Holl | |
| 2004/0018250 A1 | 1/2004 | Ceccoli et al. | |
| 2004/0052158 A1 | 3/2004 | Holl | |
| 2005/0033069 A1 | 2/2005 | Holl et al. | |
| 2007/0070805 A1 | 3/2007 | Myhrberg et al. | |
| 2007/0078062 A1 | 4/2007 | Kirsner et al. | |
| 2007/0244013 A1 | 10/2007 | Hoskins | |
| 2009/0286911 A1 | 11/2009 | Brick et al. | |

OTHER PUBLICATIONS

Written Opinion and International Search Report and dated Jun. 1, 2010 for corresponding International PCT Appln. No. PCT/US2009/063556 (8 pgs.).
Combes et al., United States Statutory Invention Registration No. H1,839 published Feb. 1, 2000.
IKA-Rotor/Stator Generators—2003 Process Catalog (38 pgs.).
Office Action dated Jun. 2, 2011 for U.S. Appl. No. 12/427,286 (12 pgs.).
Office Action dated Jun. 3, 2011 for U.S. Appl. No. 12/568,280 (16 pgs.).
Office Action dated Jun. 25, 2009 for U.S. Appl. No. 12/142,447 (10 pgs.).
Office Action dated Jan. 7, 2010 for U.S. Appl. No. 12/142,447 (6 pgs.).
Office Action dated May 13, 2010 for U.S. Appl. No. 12/142,447 (5 pgs.).
Office Action dated Feb. 4, 2010 for U.S. Appl. No. 12/492,721 (5 pgs.).
Office Action dated Feb. 18, 2010 for U.S. Appl. No. 12/635,433 (6 pgs.).
Office Action dated Feb. 18, 2010 for U.S. Appl. No. 12/635,454 (6 pgs.).
Office Action dated May 14, 2010 for U.S. Appl. No. 12/137,441 (15 pgs.).
Office Action dated Feb. 19, 2010 for U.S. Appl. No. 12/144,459 (10 pgs.).
Office Action dated Sep. 2, 2009 for U.S. Appl. No. 12/142,433 (11 pgs.).
Office Action dated Jan. 29, 2010 for U.S. Appl. No. 12/142,433 (8 pgs.).
Office Action dated May 24, 2011 for U.S. Appl. No. 12/142,433 (10 pgs.).
Office Action dated Apr. 30, 2010 for U.S. Appl. No. 12/141,191 (12 pgs.).
Office Action dated Oct. 27, 2009 for U.S. Appl. No. 12/142,120 (15pgs.).
Office Action dated May 5, 2010 for U.S. Appl. No. 12/571,537 (12 pgs.).
Office Action dated Feb. 24, 2011 for U.S. Appl. No. 12/796,358 (13 pgs.).
Office Action dated Feb. 29, 2012 for U.S. Appl. No. 12/146,733 (8 pgs.).
Office Action dated Jun. 3, 2011 for U.S. Appl. No. 12/568,155 (11 pgs.).
European Search Report dated Dec. 11, 2012 for corresponding European Application No. 09825476.6 (4 pgs.).

* cited by examiner

HIGH SHEAR PROCESS FOR PRODUCING MICRONIZED WAXES

CROSS-REFERENCE TO RELATED APPLICATIONS

This application claims benefit of U.S. Provisional Application Ser. No. 61/112,236 filed on Nov. 7, 2008, entitled "High Shear Process for Producing Micronized Waxes" incorporated herein by reference in its entirety for all purposes.

STATEMENT REGARDING FEDERALLY SPONSORED RESEARCH OR DEVELOPMENT

Not applicable.

BACKGROUND

1. Field of the Invention

This invention relates to dispersing fine particle waxes, specifically to using a high shear device to form a wax dispersion with controlled particle size.

2. Background of the Invention

Waxes, both synthetic and naturally derived, are often used in micronized or fine powder form. The particles in micronized waxes are further suspended in an organic or inorganic liquid such as water or oil. The process of micronizing wax particles is an energy intensive method that is often done in jet mills. To avoid melting of wax during milling, low temperature cryogenic gases are often employed to reduce processing temperatures thereby further increasing costs. Other techniques are also used to provide a fine-particle size wax in a liquid. Ball milling and pebble milling of waxes in a suitable solvent are often used to create a suspension of wax in solvent. These are also energy intensive techniques and require a suitable solvent (i.e. toluene, xylene) that may be undesirable for environmental and other reasons.

Micronized waxes are incorporated into scrubs to act as a mild abrasive for cleansers. European Patent EP0759971 describes the use of micronized wax in bar soap. Micronized waxes are also used in cosmetic foundation applications to provide a smooth fill for wrinkles, and for moisture resistance. For example, United States Patent Application No. 20040018250 describes some of the uses and benefits of waxes in cosmetic and pharmaceutical applications and highlights the undesirable effect of utilizing emulsifiers to incorporate wax in these applications. The inventor cites the use of high pressure to produce an emulsion. However, it is disclosed that the wax be incorporated into an organic carrier/solvent (e.g. silicone/glycol) prior to emulsifying. Thus, the final product is an emulsion and not a true dispersion of wax in a fluid. Micronized waxes are used in deodorants (U.S. Pat. No. 4,822,603) to aid in the pay-off and feel of a deodorant stick.

Micronized waxes are also used in ink, toner and coating and powder coating applications where they are dispersed in a vehicle to provide mar and abrasion resistance in such applications as over print varnish. Micronized waxes on the surface of a coating will also modify the slip properties of a coating to allow for stacking of documents without slipping. U.S. Pat. No. 5,643,984 describes the use of micronized wax in over print varnish.

Industrial and consumer coating applications also use micronized waxes to modify viscosity properties of paints as well as for their ability to reduce mar and abrasion. Pre dispersed micronized waxes are often made as a concentrate and then added to a coating. The micronized wax imparts a thixotropic viscosity profile to coatings that is beneficial in application of the coating as well as in reducing slump of the coating once applied.

Micronized waxes dispersed in a fluid have also recently found utility in oil drilling fluids due to their ability to reduce fluid loss in drilling mud. Additional benefits of using dispersed waxes in drilling fluids are their lubricating properties for the drill bit and their thixotropic properties. The plasticity of the waxes can also be controlled by addition of select solvents to the wax containing fluid. Modification of the plasticity of the waxes can aid is control of how the wax particles tend to agglomerate and form plugs in the porous drilling formation. US Patent Application No. 20070244013 describes the use of wax to reduce loss of drilling fluid. Control of wax particle size and wax melting temperature are important parameters of the wax dispersion. Various geological formations encountered during drilling of wells have different size pores, or holes in the drill shaft, through which drilling fluid can escape. Controlling wax particle size and plasticity can effectively plug these holes and significantly reduce fluid loss. There are may techniques cited for controlling drilling fluid loss. U.S. Patent no. 20070078062 describes use of an invert emulsion to form a gel that can plug the pores while drilling. These type emulsions require the use of emulsifiers that are generally undesirable in drilling fluids. Gel formation is also dependant on the ionic nature of the surrounding fluid that can vary widely in drilling fluids and can result in unstable gels. Using dispersed micronized wax avoids these issues.

Micronized wax is also used in textile lubrication to help needle and cutting processes. Micronized waxes are also used as a lubricant in metal stamping; Micronized waxes are also used as mold release agents for plastic molding. Micronized wax is used as a plastic processing aid (U.S. Pat. No. 3,997,489), Micronized waxes are used as ant blocking aids in various applications such as adhesives, rubber compounds and various plastics.

U.S. Pat. No. 3,432,483 describes the use of a continuous process for preparing finely divided polymers. The inventor describes a process that utilizes surfactant to produce small polyethylene spheres in the presence of water and high shear stirrer.

Unlike wax emulsions that form a continuous film when dried, wax dispersions retain discrete particle identity when dried from a carrier liquid. The particle size of a stable wax emulsion is also typically sub micron while the smallest micronized wax is generally greater than a micron in diameter. Thus, there is a need for direct conversion of wax into a dispersed form with a controlled particle size while minimizing energy consumption.

BRIEF SUMMARY

Use of a high shear mechanical device in a process to produce dispersed waxes. In one embodiment, the method comprises forming a dispersion of wax particles in a solvent in a high shear device prior to implementation in a waxy product. A system for producing waxy products comprising a high shear device for dispersing wax in a solvent.

A method for producing a wax product, comprising, obtaining a high shear device having at least one rotor/stator set introducing wax and a solvent into said high shear device; and forming a dispersion of wax and solvent, wherein said wax comprises particles with an average diameter between about 1 micron and about 500 microns, with most applications requiring particle size between about 5 and 30 microns and about 100 microns, and most preferably between about 10 microns and about 50 microns.

A high shear system for the production of wax product, comprising: a pump positioned upstream of a high shear device, the pump in fluid connection with a high shear device inlet; a high shear device which produces a dispersion of wax in carrier liquid, the dispersion having an average particle diameter of less than about 30 µm; and an reactor configured for the extraction of wax from the dispersion.

Thus, embodiments described herein comprise a combination of features and advantages intended to address various shortcomings associated with certain prior devices. The various characteristics described above, as well as other features, will be readily apparent to those skilled in the art upon reading the following detailed description of the preferred embodiments, and by referring to the accompanying drawings.

BRIEF DESCRIPTION OF THE DRAWINGS

For a more detailed description of the preferred embodiment of the present invention, reference will now be made to the accompanying drawings, wherein.

DETAILED DESCRIPTION OF THE PREFERRED EMBODIMENTS

Overview

Figure 1:
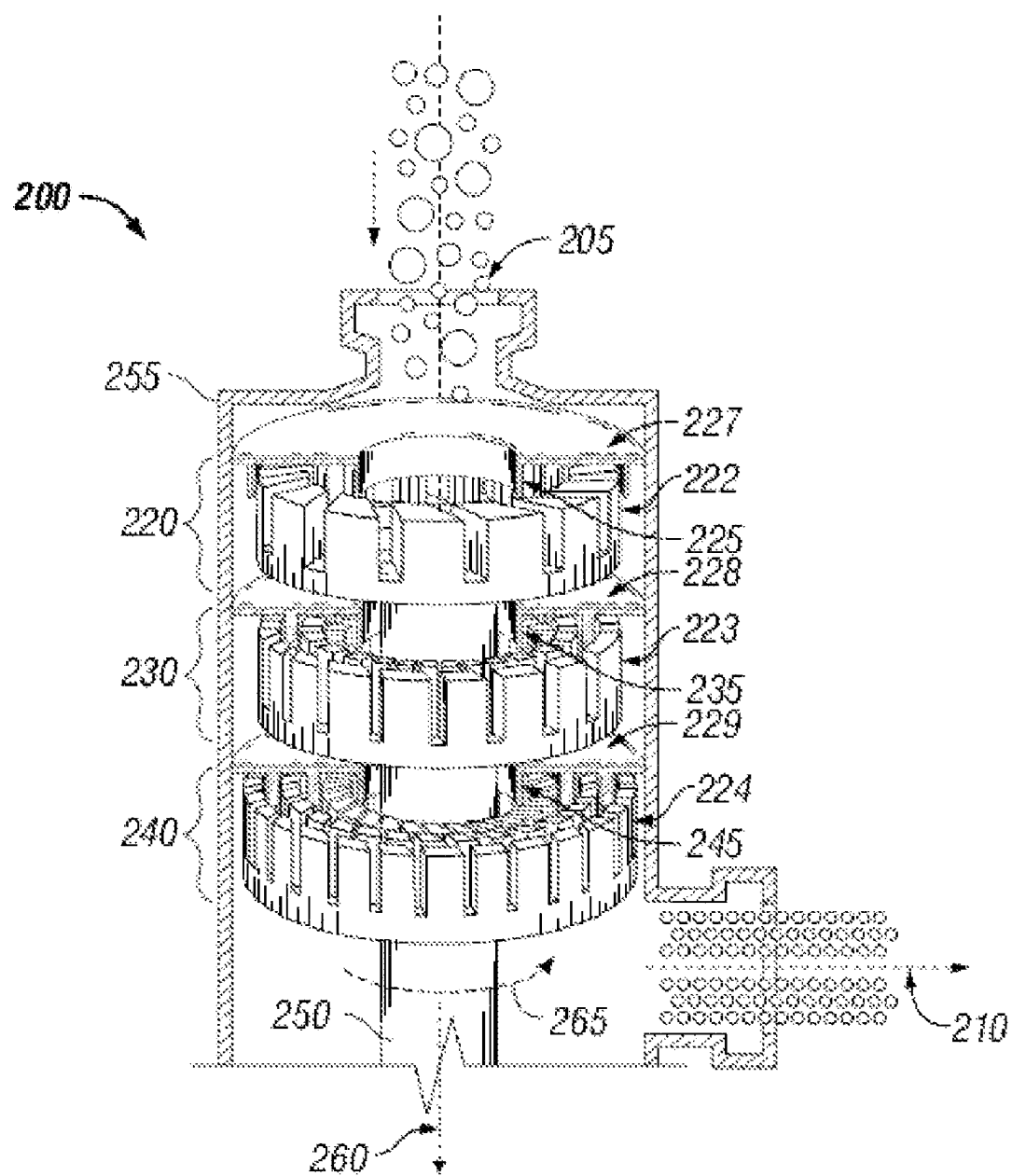
FIG. 1 is a cross-sectional diagram of a high shear device for the production of a wax dispersion in solvent.

The present disclosure provides a system and method for the dispersion of fine particulate waxes. The system and method employ a high shear mechanical device to provide rapid shearing of micron size particles in a controlled environment. Without being limited by theory, the high shear device is configured to form micron size particles of wax continuously for downstream applications. Further, a high shear device comprising rotor/stators in combination is used to disperse wax directly into a fluid medium or solvent. Upon removal of the carrier liquid, the wax particles retain their individual size and shape. Various additives may be added to the high shear dispersion such as, but not limited to plasticizers that will modify the micronized waxes are used in cosmetic and pharmaceutical topical applications.

Waxes in the present disclosure comprise any natural or synthetic wax, and in certain instances, any wax that is typified by a high degree of crystallinity and relatively sharp melting and solidification point. Natural waxes can be derived from palm, soybean, corn, castor, canola or others triglycerides. Synthetic waxes can be derived from ethylene and/or propylene with other co monomers such as vinyl acetate and maleic anhydride sometimes added to modify the final wax properties. Synthetic waxes generally range in molecular weight from about 500 to 20,000, Chemical reactions involving liquids, gases, and solids rely on the laws of kinetics that involve time, temperature, and pressure to define the rate of reactions. Where it is desirable to react raw materials of different phases (e.g. solid and liquid; liquid and gas; solid, liquid and gas), one of the limiting factors controlling the rate of reaction is the contact time of the reactants.

In conventional reactors, contact time for the reactants, such as the wax and carrier liquid, is often controlled by mixing which provides contact between the reactants and/or phases. A reactor assembly that comprises a high shear device makes possible decreased mass transfer limitations and thereby allows the dispersion to approach the theoretical kinetic limitations more closely. When dispersion rates are accelerated, residence times may be decreased, thereby increasing obtainable throughput, efficiency, and product quality.

High Shear Device

High shear devices (HSD) such as high shear mixers and high shear mills are generally divided into classes based upon their ability to mix fluids. Mixing is the process of reducing the size of inhomogeneous species or particles within the fluid. One metric for the degree or thoroughness of mixing is the energy density per unit volume that the mixing device generates to disrupt the fluid. The classes are distinguished based on delivered energy density. There are three classes of industrial mixers having sufficient energy density to create dispersions with particle or bubble sizes in the range of about 0 to about 50 µm consistently.

Homogenization valve systems are typically classified as high-energy devices. Fluid to be processed is pumped or injected under very high pressure through a narrow-gap valve into a lower pressure environment. The pressure gradients across the valve and the resulting turbulence and cavitations act to break-up and mildly shear any particles in the fluid. These valve systems are most commonly used in milk homogenization and may yield average particle size range from about 0.01 µm to about 1 µm. At the other end of the spectrum are fluid mixer systems classified as low energy devices. These systems usually have paddles or fluid rotors that turn at high speed in a reservoir of fluid to be processed, which in many of the more common applications is a food product. These systems are usually used when average particle, globule, or bubble, sizes of greater than 20 microns are acceptable in the processed fluid.

Between low energy, high shear mixers and homogenization valve systems, in terms of the mixing energy density delivered to the fluid, are colloid mills, which are classified as intermediate energy devices. The typical colloid mill configuration includes a conical or disk rotor that is separated from a complementary, liquid-cooled stator by a closely controlled rotor-stator gap, which may be in the range from about 0.25 µm to 10.0 mm. Rotors may be driven, for example, by an electric motor via direct drive, or alternatively, a belt mechanism. Many colloid mills, with proper adjustment, may achieve average particle, or bubble, sizes of about 0.01 µm to about 25 µm in the processed fluid. These capabilities render colloid mills appropriate for a variety of applications including, but not limited to: colloidal and oil/water-based dispersion processing. In certain instances, the colloid mills are can be applied to processes such as preparation of cosmetics, mayonnaise, silicone/silver amalgam, roofing-tar mixtures, and certain paint products.

Referring now to FIG. 1, there is presented a schematic diagram of a high shear device 200. High shear device 200 comprises at least one rotor-stator combination. The rotor-stator combinations may also be known as generators 220, 230, 240 or stages without limitation. The high shear device 200 comprises at least two generators, and most preferably, the high shear device comprises at least three generators. The first generator 220 comprises rotor 222 and stator 227. The second generator 230 comprises rotor 223, and stator 228; the third generator comprises rotor 224 and stator 229. For each generator 220, 230, 240 the rotor is rotatably driven by input 250. The generators 220, 230, 240 are configured to rotate about axis 260, in rotational direction 265. Stator 227 is fixably coupled to the high shear device wall 255.

The generators include gaps between the rotor and the stator. The first generator 220 comprises a first gap 225; the second generator 230 comprises a second gap 235; and the third generator 240 comprises a third gap 245. The gaps 225, 235, 245 are between about 0.25 μm ($10^{-6}$ in) and 10.0 mm (0.4 in) wide. Alternatively, the process comprises utilization of a high shear device 200 wherein the gaps 225, 235, 245 are between about 0.5 mm (0.02 in) and about 2.5 mm (0.1 in). In certain instances, the gap is maintained at about 1.5 mm (0.06 in). Alternatively, the gaps 225, 235, 245 are different between generators 220, 230, 240. In certain instances, the gap 225 for the first generator 220 is greater than about the gap 235 for the second generator 230, which is greater than about the gap 245 for the third generator 240.

Additionally, the width of the gaps 225, 235, 245 may comprise a coarse, medium, fine, and super-fine characterization. Rotors 222, 223, and 224 and stators 227, 228, and 229 may be toothed designs. Each generator may comprise two or more sets of rotor-stator teeth, as known in the art. Rotors 222, 223, and 224 may comprise a number of rotor teeth circumferentially spaced about the circumference of each rotor. Stators 227, 228, and 229 may comprise a number of stator teeth circumferentially spaced about the circumference of each stator. In embodiments, the inner diameter of the rotor is about 11.8 cm. In embodiments, the outer diameter of the stator is about 15.4 cm. In further embodiments, the rotor and stator may have an outer diameter of about 60 mm for the rotor, and about 64 mm for the stator. Alternatively, the rotor and stator may have alternate diameters in order to alter the tip speed and shear pressures. In certain embodiments, each of three stages is operated with a super-fine generator, comprising a gap of between about 0.025 mm and about 3 mm. When a feed stream 205 including solid particles is to be sent through high shear device 200, the appropriate gap width is first selected for an appropriate reduction in particle size and increase in particle surface area. In embodiments, this is beneficial for increasing catalyst surface area by shearing and dispersing the particles.

High shear device 200 is fed a reaction mixture comprising the feed stream 205. Feed stream 205 comprises a mixture or suspension of the dispersible phase and the continuous phase. The suspension comprises a liquefied mixture that contains two distinguishable substances (or phases) that will not readily mix and/or dissolve together. Without being limited by any particular theory, the suspensions have a continuous phase (or matrix), which holds therein discontinuous droplets, bubbles, and/or particles of the other phase or substance. The continuous phase may further comprise a solvent. The suspension may be highly viscous, such as slurries or pastes, with tiny particles of wax, suspended in a liquid. As used herein, the term "suspension" encompasses a continuous phase comprising a carrier liquid with poorly mixed wax dispersions. In the case where the wax is to be further oxidized or grafted, gas bubbles, particles, droplets, globules, micelles, or combinations thereof, which are insoluble in the continuous phase carrier liquid, may also be present.

Feed stream 205 may include a particulate solid component. Feed stream 205 is pumped through the generators 220, 230, 240, such that product dispersion 210 is formed. In each generator, the rotors 222, 223, 224 rotate at high speed relative to the fixed stators 227, 228, 229. The rotation of the rotors forces fluid, such as the feed stream 205, between the outer surface of the rotor 222 and the inner surface of the stator 227 creating a localized high shear condition. The gaps 225, 235, 245 generate high shear forces that process the feed stream 205. The high shear forces between the rotor and stator functions to process the feed stream 205 to create the product dispersion 210. Each generator 220, 230, 240 of the high shear device 200 has interchangeable rotor-stator combinations for producing a narrow distribution of the desired particle size, if feedstream 205 comprises a particle, or micelle size, in the product dispersion 210.

The product dispersion 210 of insoluble particles, liquid globules, or gas bubbles, in a liquid comprises a dispersion. In embodiments, the product dispersion 210 may comprise a dispersion of a previously immiscible or insoluble gas, liquid or solid into the continuous phase. The wax product dispersion 210 has an average particle, globule or bubble, size less than about 1.5 μm; in certain instances the globules are submicron in diameter. In certain instances, the average globule size is in the range from about 1.0 μm to about 0.1 μm. Alternatively, the average globule size is less than about 400 nm (0.4 μm) and most preferably less than about 100 nm (0.1 μm).

Preferably, the globules are at least micron sized. The present disclosure configures the high shear device 200 to produce micron-size wax dispersions. In embodiments, the generators 220, 230, 240 are configured to produce wax dispersions with average particle, or globules sizes ranging from about 1 micron to about 500 microns in diameter. In certain embodiments, the globule size is about 50 microns in diameter. The globule sizes are selected such that they can be controlled by the amount of shear applied to the fluid and the configuration of the generators 220, 230, 240.

Tip speed is the velocity (m/sec) associated with the end of one or more revolving elements that is transmitting energy to the reactants. Tip speed, for a rotating element, is the circumferential distance traveled by the tip of the rotor per unit of time, and is generally defined by the equation $V$ (m/sec) $= \pi \cdot D \cdot n$, where V is the tip speed, D is the diameter of the rotor, in meters, and n is the rotational speed of the rotor, in revolutions per second. Tip speed is thus a function of the rotor diameter and the rotation rate. In certain embodiments, altering the diameter or the rotational rate may increase the shear rate in high shear device 200.

For colloid mills, typical tip speeds are in excess of 23 m/sec (4500 ft/min) and may exceed 40 m/sec (7900 ft/min). For the purpose of the present disclosure the term 'high shear' refers to mechanical rotor-stator devices, such as mills or mixers, that are capable of tip speeds in excess of 1 m/sec (200 ft/min) and require an external mechanically driven power device to drive energy into the stream of products to be reacted. A high shear device combines high tip speeds with a very small shear gap to produce significant friction on the material being processed. Accordingly, a local pressure in the range of about 1000 MPa (about 145,000 psi) to about 1050 MPa (152,300 psi) and elevated temperatures at the tip are produced during operation. In certain embodiments, the local pressure is at least about 1034 MPa (about 150,000 psi). The local pressure further depends on the tip speed, fluid viscosity, and the rotor-stator gap during operation.

The shear rate is the tip speed divided by the shear gap width (minimal clearance between the rotor and stator). An approximation of energy input into the fluid (kW/l/min) may be made by measuring the motor energy (kW) and fluid output (l/min). In embodiments, the energy expenditure of a high shear device is greater than 1000 W/m³. In embodiments, the energy expenditure is in the range of from about 3000 W/m³ to about 7500 W/m³.

The high shear device 200 combines high tip speeds with a very small shear gap to produce significant shear on the material. The amount of shear is typically dependent on the viscosity of the fluid and the shear gap. The shear rate generated in a high shear device 200 may be greater than 20,000

$s^{-1}$. In embodiments, the shear rate generated is in the range of from 20,000 $s^{-1}$ to 100,000 $s^{-1}$. The shear rate generated in HSD 40 may be in the greater than 100,000 s−1. In some embodiments, the shear rate is at least 500,000 s−1. In some embodiments, the shear rate is at least 1,000,000 s−1. In some embodiments, the shear rate is at least 1,600,000 s−1. In embodiments, the shear rate generated by HSD 40 is in the range of from 20,000 s−1 to 100,000 s−1. For example, in one application the rotor tip speed is about 40 m/s (7900 ft/min) and the shear gap width is 0.0254 mm (0.001 inch), producing a shear rate of 1,600,000 s−1. In another application, the rotor tip speed is about 22.9 m/s (4500 ft/min) and the shear gap width is 0.0254 mm (0.001 inch), producing a shear rate of about 901,600 s−1.

The rotor is set to rotate at a speed commensurate with the diameter of the rotor and the desired tip speed as described hereinabove. Transport resistance is reduced by incorporation of high shear device 200 such that the dispersion and reaction rate is increased by at least about 5%. Alternatively, the high shear device 200 comprises a high shear colloid mill that serves as an accelerated rate reactor. The accelerated rate reactor comprises a single stage, or dispersing chamber in certain instances. Further, accelerated rate reactor comprises a multiple stage, inline disperser comprising at least 2 stages.

Selection of the high shear device 200 is dependent on throughput requirements and desired particle or bubble size in the outlet dispersion 210. In certain instances, high shear device 200 comprises a Dispax Reactor® of IKA® Works, Inc. Wilmington, N.C. and APV North America, Inc. Wilmington, Mass. Model DR 2000/4, for example, comprises a belt drive, 4M generator, PTFE sealing ring, inlet flange 1" sanitary clamp, outlet flange ¾" sanitary clamp, 2 HP power, output speed of 7900 rpm, flow capacity (water) approximately 300 l/h to approximately 700 l/h (depending on generator), a tip speed of from 9.4 m/s to above about 41 m/s (about 1850 ft/min to above about 8070 ft/min). Several alternative models are available having various inlet/outlet connections, horsepower, tip speeds, output rpm, and flow rate. In further instances, the high shear device 200 comprises any device with configurable to produce the high shear rate and throughput for forming a wax dispersion.

Without wishing to be limited to any particular theory, it is believed that the degree of high shear mixing in a high shear device is sufficient to increase rates of mass transfer. Further, a high shear device may produce localized non-ideal conditions that enable reactions to occur that would not otherwise be expected to occur based on Gibbs free energy predictions. Additionally, such reactions would not be expected at low shear mixing parameters. Localized non-ideal conditions are believed to occur within the high shear device resulting in increased temperatures and pressures with the most significant increase believed to be in localized pressures. The increase in pressures and temperatures within the high shear device are instantaneous and localized. In certain instances, the temperature and pressure increases revert to bulk or average system conditions once exiting the high shear device. In some cases, the high shear-mixing device induces cavitation of sufficient intensity to dissociate one or more of the reactants into free radicals, which may intensify a chemical reaction or allow a reaction to take place at less stringent conditions than might otherwise be required. Cavitation may also increase rates of transport processes by producing local turbulence and liquid microcirculation (acoustic streaming). An overview of the application of cavitation phenomenon in chemical/physical processing applications is provided by Gogate et al., "Cavitation: A technology on the horizon," *Current Science* 91 (*No.* 1): 35-46 (2006). The high shear-mixing device of certain embodiments of the present system and methods is operated under what are believed to be cavitation conditions that might be useful in reactions involving the oxidation of dispersed micronized wax or in such grafting reactions as maleation of wax using peroxide catalyst.

Description of High Shear Process and System for Production of Micronized Wax

Figure 2:
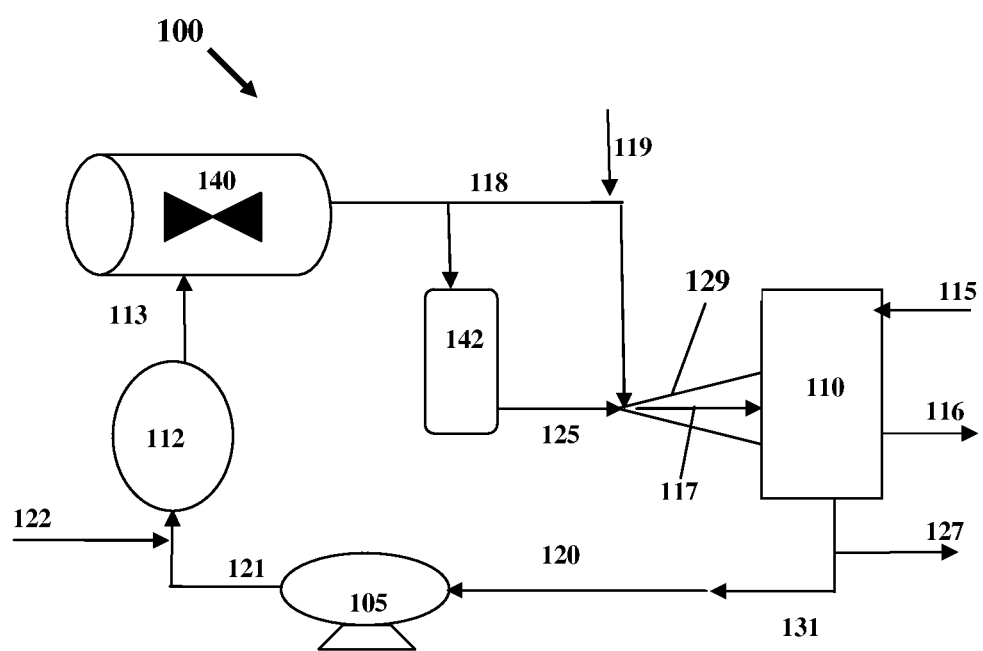
FIG. 2 illustrates a schematic diagram of a system for the production of a wax dispersion in a solvent.

High Shear System 100, hereinafter HSS 100, is configured for the dispersion of wax into a carrier liquid. FIG. 2 illustrates a flow diagram of an embodiment for the dispersion process comprising a high shear device. The disclosed process with the high shear device enhances the conversion by improving dispersion of wax into a carrier liquid. FIG. 2 illustrates the basic components of HSS 100 including pump 105, high shear device (hereinafter HSD) 140, and reactor 110. In certain embodiments, the HSD 140 is positioned between pump 105 and reactor 110. Pressurization of make up liquid can be at any suitable point in the process 100 and feeds HSD 140 via pump outlet stream 121

In certain instances, HSS 100 may combine high shear, high pressure, and/or high temperature to enable the molten wax to disperse in the carrier liquid by HSD 140. Wax may be combined with other ingredients including stabilizers, anti-oxidants, plasticizers, colorants, dyes, pigments and other ingredients prior to dispersing or solubilizing in the carrier fluid. Pump inlet stream 120 comprises any suitable organic or inorganic liquid suitable for the end use application being targeted. For examples, the carrier liquid utilized is a solution where the wax has a low solubility. In certain embodiments, water may be used where the final wax dispersion is to be used in water based systems. Exemplary aqueous systems include water based inks and coatings. Organic liquids may be used in such applications as oil based drilling fluids.

In embodiments, pump 105 increases the pressure of pump inlet stream 120 to greater than about 203 kPa (2 atm). Alternatively, pump 105 increases the pressure to greater than about 2025 kPa (20 atm) prior to pump outlet stream 12. Preferably, all contact parts of pump 105 are stainless steel, for example, type 316 stainless steel. Pump 1055 may be any suitable pump, for example, a Roper Type 1 gear pump, Roper Pump Company (Commerce Ga.) or a Dayton Pressure Booster Pump Model 2P372E, Dayton Electric Co (Niles, Ill.). The increased pressure of pump outlet stream 121 can be used to accelerate reactions with the limiting factor being the pressure limitations of pump 105 and high shear device 140.

Pump outlet stream 121 is in fluid communication with HSD inlet stream 113. Pump outlet stream 121 may be continuous with HSD inlet stream 113. In certain embodiments, HSD inlet stream 113 comprises pump outlet stream 121. HSD inlet stream 113 is in fluid communication with the HSD 140. In certain embodiments, HSD inlet stream 113 comprises pump outlet stream 121, which optionally, has undergone further processing, for example heating or cooling.

Dispersible reactant stream 122 is injected into pump outlet stream 121. Dispersible stream 122 comprises wax, in certain instances, a molten wax. In further embodiments, dispersible stream 122 comprises wax globules, wax particles, wax grains, wax micelles, or the like without limitation. In certain embodiments, dispersible stream 122 comprises a mixture of wax particles, molten wax, and wax micelles in a suitable carrier liquid. In alternative embodiments, HSD inlet stream 113 and dispersible reactant stream 122 may be injected separately into HSD 140. For example, it can be envisioned that the wax in dispersible stream 122 enters HSD 140 separately from HSD inlet stream 113 comprising pump outlet stream 121. In certain instances, pump outlet stream 121 is heated to a temperature at about or above the melting point of the wax by a heater 112. Heater 112 comprises any device configurable to raise the temperature to about or above the melting temperature of the wax. Without wishing to be limited by theory, increasing the temperature of the wax increasing the plasticity of the wax. Increasing the temperature improves the motility of the wax in the carrier liquid in HSD inlet stream 113.

HSD inlet stream is in fluid communication with HSD 140. HSD 140 intimately mixes the wax suspension in dispersible stream 122 with pump outlet stream 121. HSD 140 creates a fine wax particle dispersed wax stream 122 within high shear inlet stream 113. As discussed in detail above, HSD 140 is a mechanical device that utilizes, for example, a stator-rotor mixing head with a fixed gap between the stator and rotor. HSD 140 combines high tip speeds with a very small shear gap to produce significant shear on the material being processed. The amount of shear will be dependant on the viscosity of the carrier liquid and wax. In HSD 140, the wax and carrier liquid are mixed to form dispersion comprising about 1 micron diameter wax globules dispersed in the carrier liquid. In certain instances, the HSD 140 will form a wax dispersion in the carrier liquid having globules of wax with sub-micron diameters, and further, in certain applications, the globules will have a diameter of less than about 100 nanometers. In certain instances, multiple HSD 140 are in fluid communication with HSD inlet stream 113. Further, use of multiple high shear mixers aligned in series, and in instances with varying shear rates, is contemplated to further enhance the reaction. Alternatively, a plurality of HSD 140 arranged in parallel may be used to increase the volume of wax dispersed in the carrier liquid.

Figure 3:
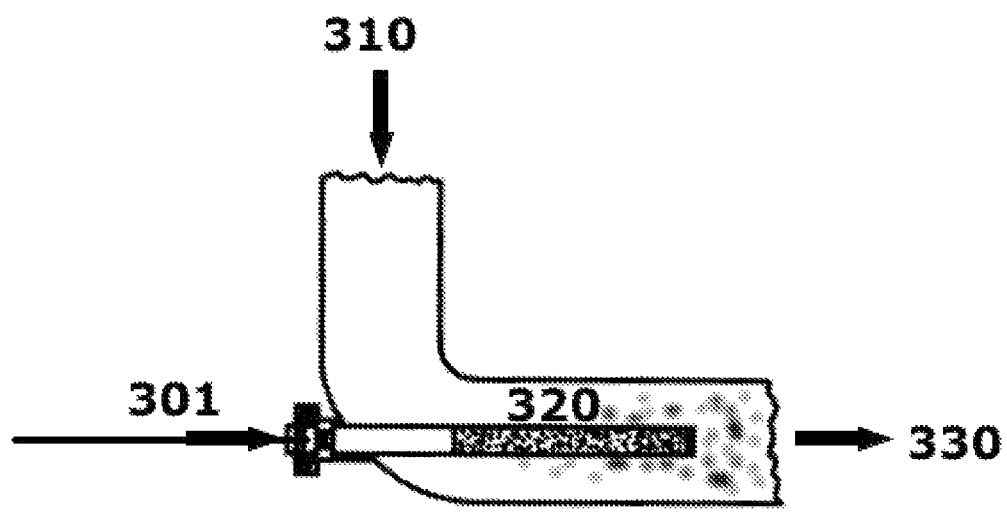
FIG. 3 illustrates an apparatus for introducing molten wax into a high shear device inlet.

In order for the HSD 140 to form a uniform dispersion of micron-sized wax in the carrier liquid, the molten wax may be pre-dispersed in the carrier liquid in such a way that it will not restrict flow to and through the HSD 140. For this reason, it is desirable to pre-disperse the liquid wax in the carrier liquid. FIG. 3 illustrates an embodiment of a device to pre-disperse the wax in the carrier liquid stream 310 by means of a sparging device or sparger 320 incorporated within a section of pipe where the carrier liquid is flowing. Sparger 320 comprises a vessel, having passages disposed within a conduit. Liquid wax stream 301 is injected into sparger 320, or otherwise forced though the sparger 320 for pre-dispersion into liquid carrier stream 310. The resulting pre-dispersion stream 330 can then be fed into the HSD 140 where the high-shear creates micron-size wax dispersion. Suitable spargers 320 can be manufactured out of pipe with drill holes, or manufactured using sintered metal. Suitable sparging devices may be for example, manufactured by Mott Corporation, Farmington, Conn. Any suitable sparger 320 that will create pre-dispersion wax droplets within the pre-dispersion stream 330 would be suitable.

Referring again to FIG. 2, HSD 140 is in fluid communication with reactor 110 via HSD exit stream 118. In certain embodiments, HSD outlet stream 118 may be heated or cooled prior to introduction to reactor 110. In certain instances, the use of external heat exchangers 142 for heating and/or cooling is within the scope of one of more of the embodiments described and claimed herein. Examples of exchangers may preferably include, without limitation, shell and tube, plate, and coil heat exchangers, as will be known to those of skill in the art. In further embodiments, HSD exit stream 118 is introduced to heat exchanger 142 to shock cool the dispersion to a temperature sufficient to solidify the dispersed wax. In certain instance, low fouling exchangers are preferred to allow wax particle passage therethrough. Alternatively, cooling can also be accomplished by addition of make up liquid stream 119 that is injected at a temperature below that required to keep the dispersed wax molten. Any suitable liquid may be utilized for make up liquid stream 119, providing a low solubility of the wax in the liquid. Exchanger exit stream 125 may comprise a component of HSD exit stream that feeds reactor 110. Alternatively, expansion nozzle 129 is any suitable to quench molten dispersed wax globules. The carrier liquid and dispersed molten wax comprising HSD exit stream 118 is passed through an expansion nozzle 129 where the temperature of the dispersed wax and carrier liquid is rapidly cooled to below the melting point of the wax.

After processing by heat exchanger 142, HSD outlet stream 118 comprising exchanger exit stream 125 is injected into inlet stream 117 for introduction to reactor 110 via expansion nozzle 129. HSD outlet stream 119, exchanger exit stream 125 and inlet stream 117 may be the same stream. In further embodiments, HSD outlet stream 118 and/or exchanger exit stream may be recycled through the HSD 140 prior to introduction to inlet stream 117.

Inlet stream 117 is in fluid communication with reactor 110. Reactor 110 is any type of reactor in which the dispersed wax in solvent or carrier liquid is continued and modulated. Further, reactor 10 is preferably configured to separate wax from the carrier liquid. Reactor 110 may comprise a continuous stirred tank reactor or a batch reactor, without limitation, to extract wax from carrier liquid. In certain embodiments, reactor 110 is configured as a holding tank for increased residence time, agitation, and/or separation of the wax dispersion. Further, reactor 110 may preferably comprise a jacketed reactor to continue cooling the wax dispersion.

Reactor 110 further comprises additional conduits comprising supplemental inlet 115, liquid product stream 116, dry product stream 127, and recycle stream 131. Supplemental inlet 115 is configured for the addition of modifiers, plasticizers, additives, and the like without limitation. These compounds may improve the quality of liquid product stream 116 and dry product stream 127. Liquid product stream 116 may be removed from reactor 110 by heating, evaporation, vacuum, super-critical fluid extraction, centrifuge, or other means as known to one skilled in the art. Liquid product stream 116 may comprise, without limitation, an ink, a stain, a paint, a film, or other waxy solution without limitation. Dry product stream 127 may comprise a powder, a particulate media, a dry paint, a plastic, a polymer, or other dry wax product without limitation. Additional processing to remove further liquid, such as remaining carrier liquid may be conducted along dry product stream 127. In certain instances, removed carrier liquid comprises recycle stream 131. Further, recycle stream 131 may be coupled, directly or indirectly, to pump inlet stream 120.

In certain instances, the wax globules in HSD 140 and reactor 110 may be exposed to additional compounds for further processing. In embodiments, the wax globules may be exposed to an oxidant, such as oxygen, ozone, peroxide, or others known to one skilled in the art. Alternatively, the wax globules are exposed to maleic anhydride and a peroxide catalyst for grafting.

While the preferred embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. Accordingly, the scope of protection is not limited by the description set out above, but is only limited by the claims that follow, that scope including all equivalents of the subject matter of the claims.

We claim:

1. A method for producing a wax product, comprising:
   operating a high shear device having at least one rotor/stator, configurable for a shear rate of at least 20,000 s$^{-1}$;
   introducing wax and a carrier liquid into said high shear device;
   forming with the high shear device a dispersion of wax in a carrier liquid, wherein the wax comprises globules with an average diameter less than 500 microns;
   exposing the wax globules to maleic anhydride and a catalyst;
   quenching the dispersion below a wax melting point; and
   transferring the quenched dispersion to a reactor, wherein wax is extracted from the carrier liquid in the reactor resulting in a dry wax product stream and a liquid product stream.

2. The method of claim 1 wherein introducing the wax to the high shear device comprises raising the temperature of the wax.

3. The method of claim 1 wherein the average diameter is also greater than 125 microns.

4. The method of claim 1, wherein the carrier liquid is water, and wherein the catalyst is peroxide.

5. The method of claim 1 wherein the dispersion comprises immiscible wax globules dispersed in the carrier liquid.

6. The method of claim 1, wherein the at least one rotor/stator is configured with a gap clearance therebetween in the range of about 0.025 mm to about 10.0 mm.

7. The method of claim 6 wherein the rotor/stator set operates at a shear rate of at least about 100,000 s$^{-1}$.

8. The method of claim 1, wherein the carrier liquid is water.

9. The method of claim 1 further comprising heating the temperature of the wax to above about the wax melting temperature prior to introduction to the high shear device.

10. The method of claim 1, wherein the carrier liquid is water.

11. The method of claim 1, wherein the catalyst is peroxide catalyst.

12. The method of claim 1 further comprising using the dry wax product in drilling fluid.

13. The method of claim 1, wherein the wax is derived from palm, soybean, corn, castor, or canola.

14. The method of claim 1, wherein the high shear device is configured with a second rotor and a second stator configured therein, and wherein each of the second rotor and the second stator have a toothed surface.

15. The method of claim 14, wherein the second rotor and the second stator operate conjunctively at a shear rate greater than the at least one rotor/stator.

16. A method for producing a wax product, comprising:
    operating a high shear device having at least one rotor/stator, wherein the high shear device is configured to operate at a shear rate of at least 20,000 s$^{-1}$;
    introducing wax and a carrier liquid into said high shear device; and
    forming with the high shear device a dispersion of wax in a carrier liquid, wherein the wax comprises globules with an average diameter less than 500 microns; and
    grafting the wax globules by exposing the wax globules to maleic anhydride and a peroxide catalyst.

17. The method of claim 16 further comprising oxidizing the wax globules in the high shear device.

18. A method for producing a wax product, comprising:
    injecting wax into water to form a mixture consisting of wax and water;
    processing the mixture in a high shear device at a shear rate of at least 20,000 s$^{-1}$ to form a processed mixture, wherein the processed mixture comprises wax globules with an average diameter less than 500 microns; and
    extracting wax from the processed mixture in a reactor resulting in the wax stream and a liquid product.

19. The method of claim 18, the method further comprising exposing the wax globules to maleic anhydride and a catalyst.

* * * * *